US007066181B2

(12) United States Patent
West

(10) Patent No.: US 7,066,181 B2
(45) Date of Patent: Jun. 27, 2006

(54) BODY SUPPORT HARNESS

(75) Inventor: R. Gary West, Birmingham, AL (US)

(73) Assignee: HealthSouth Corp., Birmingham, AL (US)

( * ) Notice: Subject to any disclaimer, the term of this patent is extended or adjusted under 35 U.S.C. 154(b) by 347 days.

(21) Appl. No.: 10/873,954

(22) Filed: Jun. 22, 2004

(65) Prior Publication Data

US 2004/0230150 A1 Nov. 18, 2004

Related U.S. Application Data

(63) Continuation-in-part of application No. 10/082,153, filed on Feb. 26, 2002, now Pat. No. 6,752,776.

(51) Int. Cl.
*A61F 5/37* (2006.01)

(52) U.S. Cl. .......................... 128/875; 601/23; 607/49; 128/869; 128/876; 482/69; 482/54

(58) Field of Classification Search ................. 128/869, 128/870, 873, 874, 875, 876, 99.1, 100.1; 482/54, 51, 69, 66; 601/23, 33, 34, 35; 607/48, 607/49

See application file for complete search history.

(56) References Cited

U.S. PATENT DOCUMENTS

| | | | | | |
|---|---|---|---|---|---|
| 2,719,568 | A | * | 10/1955 | Webb | 482/68 |
| 4,303,041 | A | * | 12/1981 | Thompson et al. | 482/66 |
| 4,512,437 | A | | 4/1985 | Savage | |
| 4,905,678 | A | | 3/1990 | Cumins et al. | |
| 4,941,497 | A | * | 7/1990 | Prather et al. | 135/67 |
| 4,981,307 | A | * | 1/1991 | Walsh | 280/290 |
| 5,360,082 | A | * | 11/1994 | Bell | 182/3 |
| 5,502,851 | A | | 4/1996 | Costello | |
| 5,503,621 | A | | 4/1996 | Miller | |
| 5,620,412 | A | * | 4/1997 | Modglin | 602/24 |
| 5,660,445 | A | | 8/1997 | Murray | |
| 5,695,432 | A | | 12/1997 | Soderlund | |
| 5,765,738 | A | | 6/1998 | Hoffner | |
| 5,814,001 | A | | 9/1998 | Schwenn et al. | |
| 5,893,367 | A | | 4/1999 | Dubatas et al. | |
| 5,951,591 | A | * | 9/1999 | Roberts | 606/241 |
| 6,039,707 | A | | 3/2000 | Crawford et al. | |
| 6,264,584 | B1 | | 7/2001 | Bass | |
| 6,436,011 | B1 | * | 8/2002 | Cook | 482/69 |
| 6,500,137 | B1 | | 12/2002 | Molino et al. | |
| 6,578,594 | B1 | | 6/2003 | Bowen et al. | |
| 6,588,022 | B1 | | 7/2003 | Anders et al. | |
| 6,689,075 | B1 | | 2/2004 | West | |
| 6,752,776 | B1 | | 6/2004 | West | |

* cited by examiner

*Primary Examiner*—Henry Bennett
*Assistant Examiner*—Camtu Nguyen
(74) *Attorney, Agent, or Firm*—Bradley, Arant, Rose & White

(57) ABSTRACT

A torso support portion and a pair of thigh support portions are each formed of an outer layer of hard relatively stiff molded plastic material of limited flexibility and an inner layer of relatively soft cushioning material for distributing the weight of a patient over a large area. The torso support portion may comprise a rear panel adjustable secured between two body panels. Tightening straps serve to tighten the torso support portion about a patient with the parts of the torso support portion adjacent the front opposite free sides of the two body panels overlapping one another in operative position. A pair of tightening straps serve to tighten each of the thigh support portions about the thighs of a patient with the free sides of each thigh support portion spaced a substantial distance from one another in operative position. Four adjustable suspension straps are provided for suspending the torso support portion and provide a quick-release feature. Two adjustable groin straps are provided for stabilizing the torso support portion. Each of the thigh support portions is connected to the torso support portion in depending relationship therefrom by adjustable connecting straps. One of the thigh support portions is provided with a channel extending from the top edge to the bottom edge thereof portion for receiving a catheter. The thigh support portions are provided with outwardly facing fastening portions for fastening the thigh support portions to a powered gait orthosis device.

26 Claims, 5 Drawing Sheets

BODY SUPPORT HARNESS

The instant patent application is a continuation-in-part of U.S. patent application Ser. No. 10/082,153 filed Feb. 26, 2002, now U.S. Pat. No. 6,752,776. The present invention relates to a body support harness which is particularly adapted to support the weight of the body of a patient on a powered gait orthosis device such as that disclosed in co-pending U.S. patent application Ser. No. 09/938,825 (now U.S. Pat. No. 6,689,075), Ser. Nos. 10/200,453 and 10/749,391, the disclosures of which are incorporated herein by reference. Such devices aid in research and rehabilitation of non-ambulatory patients and provide therapeutic exercise for those with spinal cord injuries.

BACKGROUND OF THE INVENTION

The present invention is an improvement over the harness construction as shown in U.S. Pat. No. 5,502,851 which is specifically designed for supporting the weight of the body of a patient on a device used for rehabilitation and physical therapy purposes. This prior art harness is made from soft fabric material which causes serious problems in use. The fabric which forms the lumbar support belt and the thigh wraps of this prior art harness tends to bunch up when supporting the weight of a patient so that undesirable areas of high pressure are created in localized areas on the patients body. Accordingly, the patient's weight is not well distributed and there is a tendency for the harness material to pinch the skin of the patient. This is, of course, very undesirable.

Furthermore, the patented harness employs a pair of shoulder straps which tend to squeeze the shoulders of the patient when suspended in the harness.

SUMMARY OF THE INVENTION

A primary objective of the present invention is to overcome the disadvantages of the prior art device discussed above and provide a harness which successfully distributes the weight of the patient over a wide area and prevents any bunching up of the weight supporting portions of the harness disposed adjacent the patient's body, and which eliminates pinching of the patient's skin. Additionally, the suspension strap means of the harness prevents any squeezing of a patient's shoulders when suspended within the harness. Finally, the disclosed harness provides multiple adjustment mechanisms to provide superior fit and comfort to the patient while the harness is in the operative position.

In one embodiment, the harness of the invention comprises a torso support portion and a pair of thigh support portions which are connected to the torso support portion and depend there from. The torso support portion may be fashioned as a single piece (as shown in co-pending U.S. patent application Ser. No. 10/082,153, now U.S. Pat. No. 6,752,776, the disclosure of which is incorporated hereby by reference) or in more than one piece. In one embodiment, the torso support portion incorporates two body panels and a rear panel adjustably secured between the two body panels to allow increased adjustment of the body harness disclosed. Each of the torso and thigh support portions is formed of an outer layer of hard relatively stiff molded plastic material of limited flexibility and an inner layer of relatively soft cushioning material. In addition, one or both of the torso and thigh support portions may further comprise a removable lining of a relatively soft cushioning material. This construction ensures that there will be no bunching up of these components when supporting a patient, thereby distributing the weight over a wide area and preventing pinching of the patient's skin. Although the outer layer is hard, the inner layer and removable lining (if incorporated) is sufficiently soft so that it can conform to the contours of a patient's body and will be comfortable in use.

As discussed above, in one embodiment the torso support portion comprises two body panels and a rear panel adjustably secured between the two body panels. The rear panel has opposite free sides and the two body panels each have a rear free side and a front free side. The torso support portion is constructed and arranged so that the parts of the two body panels adjacent to the front free sides thereof overlap one another in operative position on the torso of a patient. The parts of the two body panels adjacent to the rear free sides do not overlap one another, but may overlap parts of the rear panel. This arrangement ensures that the torso of the patient will not be pinched and the patient's weight is distributed over a maximum area of the torso support portion. Furthermore, this arrangement provides for increased adjustability of the body harness.

The thigh support portions of the invention each have opposite free sides, but these support portions which have a lesser weight support function than the torso support portion are so constructed and arranged that the free sides thereof are spaced from one another a substantial distance when in the operative position to ensure that the thighs of a patient will not be pinched.

The suspension strap means of the present harness include a plurality of suspension straps. In one embodiment, there are four suspension straps which are spaced apart and connected to the torso support portion at spaced points. The suspension straps are disposed substantially vertically from the torso support portion and are spaced from the shoulders of a patient, thereby ensuring that there will be no squeezing of the shoulders when the harness is in operative position. The harness disclosed may also comprise a plurality of groin straps. In one embodiment, the groin straps comprise two spaced apart groin straps which are connected to the torso support portion at spaced points. One end of each groin strap is attached to the front portion of the torso support (in one embodiment, adjacent to the front free sides of the two body panels) and the other end is attached to the back portion of the torso support portion (in one embodiment, adjacent to the opposite free sides of the rear panel). The groin straps may incorporate a padding member to increase the comfort during wear. Each groin strap is spaced around the groin of the patient, thereby ensuring that there will be no or minimal displacement of the torso support portion in the upward direction when the body harness is in used in an operative position.

Since the thigh support portions include an outer layer formed of a hard relatively stiff molded plastic material of limited flexibility, a special provision may be made to accommodate a catheter which is often present when treating patients with spinal cord injuries and the like. Normally, the patient will wear some sort of pants, and if a catheter is present, it will be under the pants. Therefore, it is necessary to provide a channel extending from the top edge to the bottom edge of at least one of the thigh support portions for receiving the material of the pants and the catheter so that the catheter is not damaged during use of the harness. Such a channel is provided as an integral part of at least one of the thigh support portions of the harness.

Additionally, the thigh support portions are provided on the outer surface thereof with fastening portions for fastening the thigh support portions to a powered gait orthosis device, such as those referenced above.

DETAILED DESCRIPTION

Figure 1:
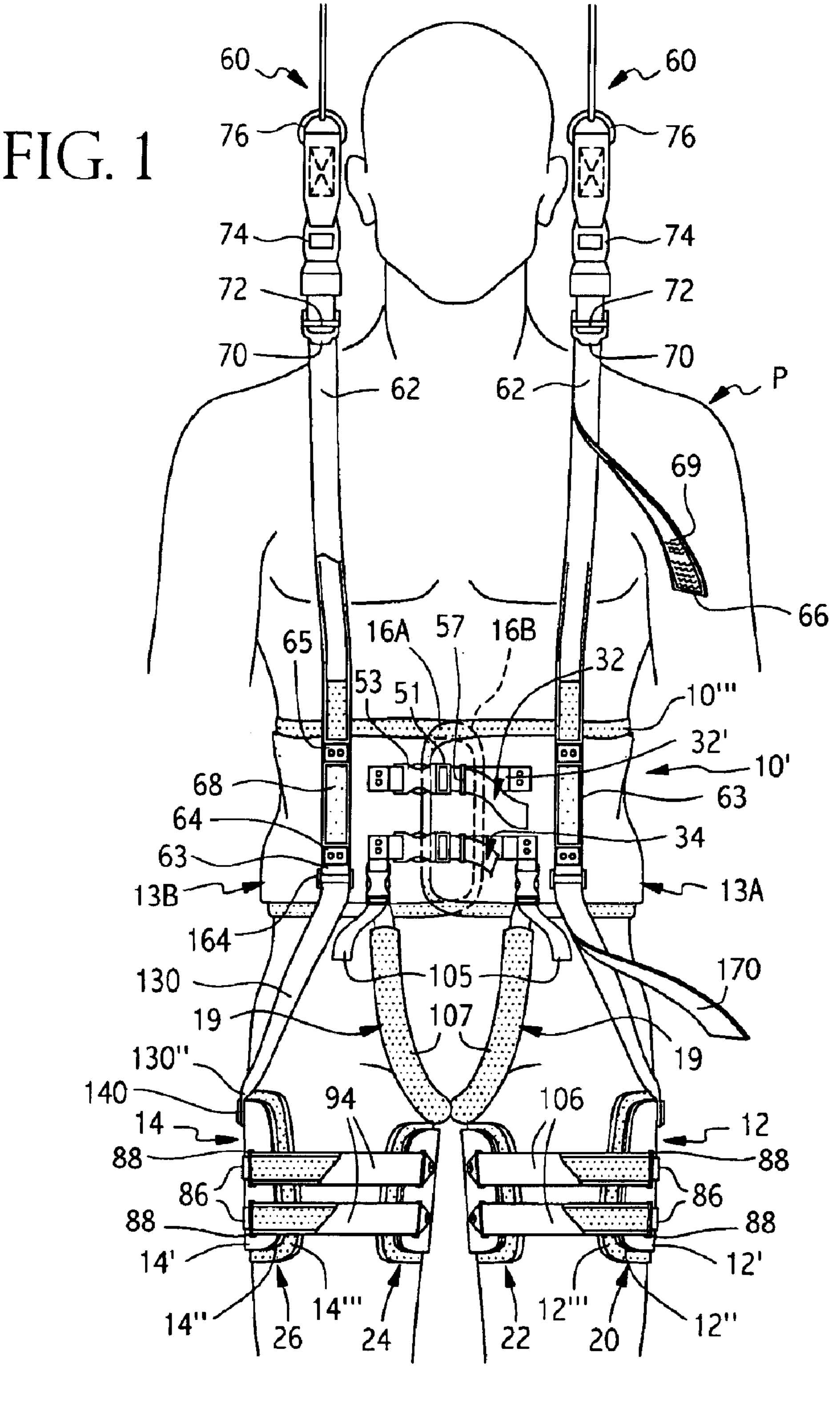
FIG. 1 is a front view of one embodiment of the body harness mounted in operative position upon the body of a patient.

Referring now to the drawings wherein like reference characters designate corresponding parts throughout the several views, a patient P is shown with the disclosed harness mounted in operative position on his body. In one embodiment, the harness includes a torso support portion 10, and a pair of thigh support portions 12 and 14. In one embodiment, the torso support portion comprises multiple components, including a rear panel 11 and two body panels 13A and 13B. The rear panel 11 has opposite free side 15A and 15B and is adjustably secured between the two body panels 13A and 13B. The two body panels 13A and 13B are substantially identical and extend around the side of the torso of the patient P. The two body panels 13A and 13B each have a front free side 16A and 16B, respectively, and a rear free side 18A and 18B, respectively. The torso portion is adjustable to fit the circumference of the torso of the patient P. The torso support portion 10 may further comprise a pair of groin straps 19 which aid in stabilizing the torso support portion 10.

Figure 3A:
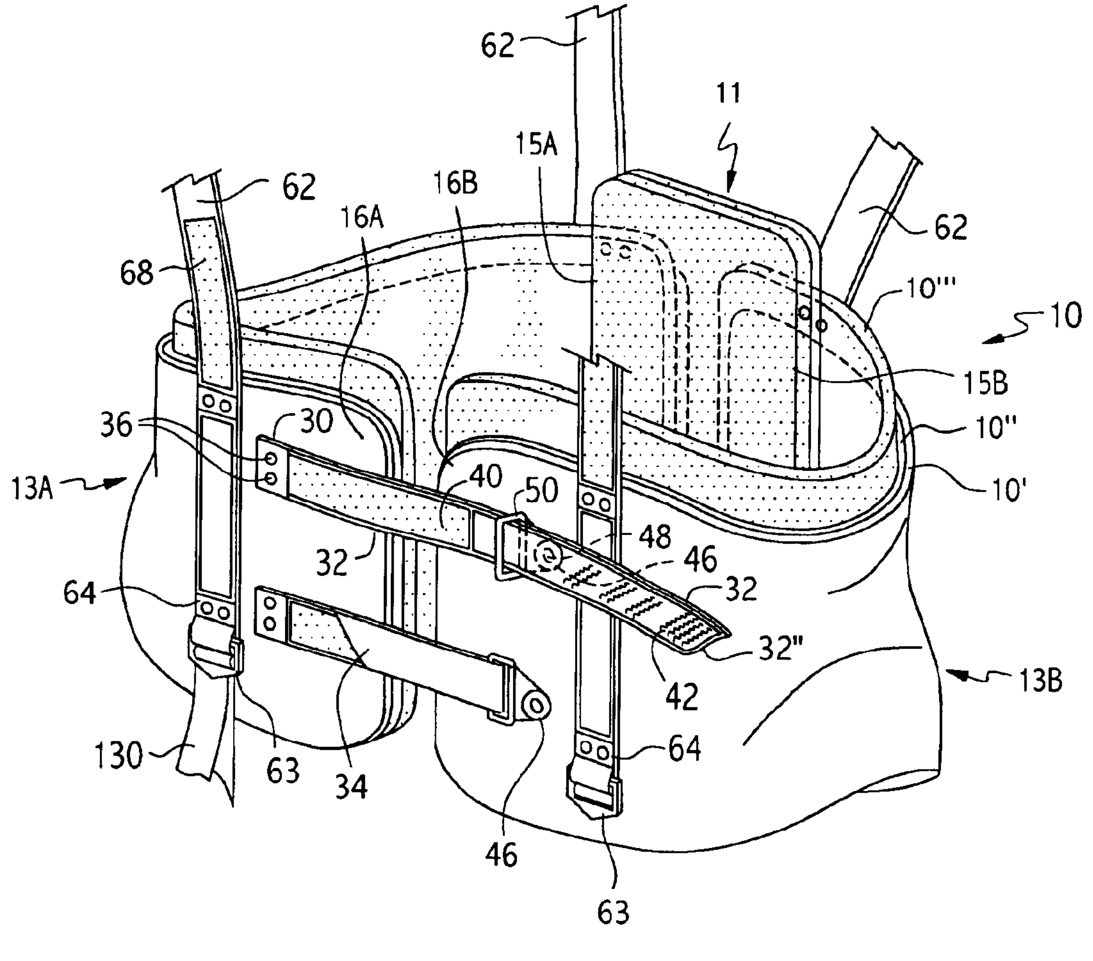
FIG. 3A is a top perspective view of the torso support portion of the harness prior to mounting on a patient.
Figure 3B:
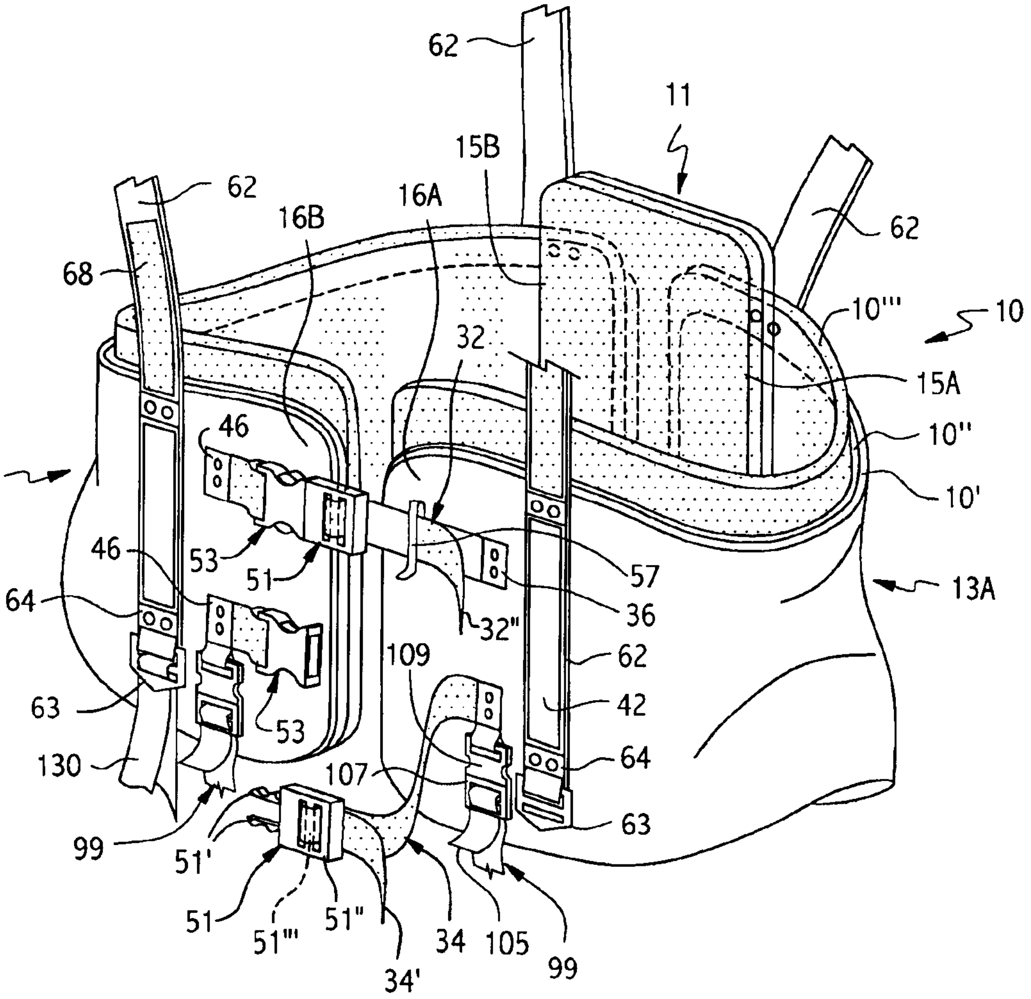
FIG. 3B is a top perspective view of an alternate embodiment of the torso support portion of the harness.

In one embodiment, the torso support portion 10 is formed of an outer layer 10', and an inner layer 10", and may further comprise a removable liner 10'" (see FIGS. 3A and 3B for detail). The inner layer 10" is vulcanized to the outer layer 10' or otherwise affixed thereto. The removable liner 10'" is removably coupled to the inner layer 10" so that the removable liner 10'" can be removed for cleaning after use of the torso support portion 10 by a patient P. The outer layer 10' is formed of a hard relatively stiff molded plastic material of limited flexibility. In one embodiment, this material is PETROTHENE, a medium density polyethylene manufactured by Equistar Chemicals of Houston Tex. This plastic material has a density nominal value of 0.930 g/cc. The inner layer 10" is formed of a relatively soft cushioning material. In one embodiment, this cushioning material is pure gum sponge rubber in the form of elastic, open cell sheeting. The cushioning material has a density of 22 lbs/cu ft and has a Durometer hardness, Shore 00 of 30–50. The cushioning material also has compression (25% deflection) of 2–5 psi and tensile strength of 2–5 psi. The removable liner 10'" is formed from a soft plastic or similar material. The combination of these outer layer 10' and inner layer 10" enables the torso support portion to distribute the weight of the patient over a wide area while providing a comfortable fit for the patient. Additionally, the incorporation of the removable liner 10'" (if used) allows the simplified maintenance of the torso support portion 10 by allowing the unit to be easily cleaned between uses.

The pair of thigh support portions 12 and 14 are also formed of outer layers 12' and 14' respectively and inner layers 12" and 14" respectively. The thigh support portions 12 and 14 may further comprise a removable liner 12'" and 14'" respectively. These outer and inner layers and removable liner are secured to one another in the same manner as in the torso support portion. The outer and inner layers and the removable liner of the thigh support portions are formed of the same material as the outer and inner layers respectively of the torso support portion. For clarity, the removable liner 12'" is not shown in FIGS. 4 and 5.

Figure 2:
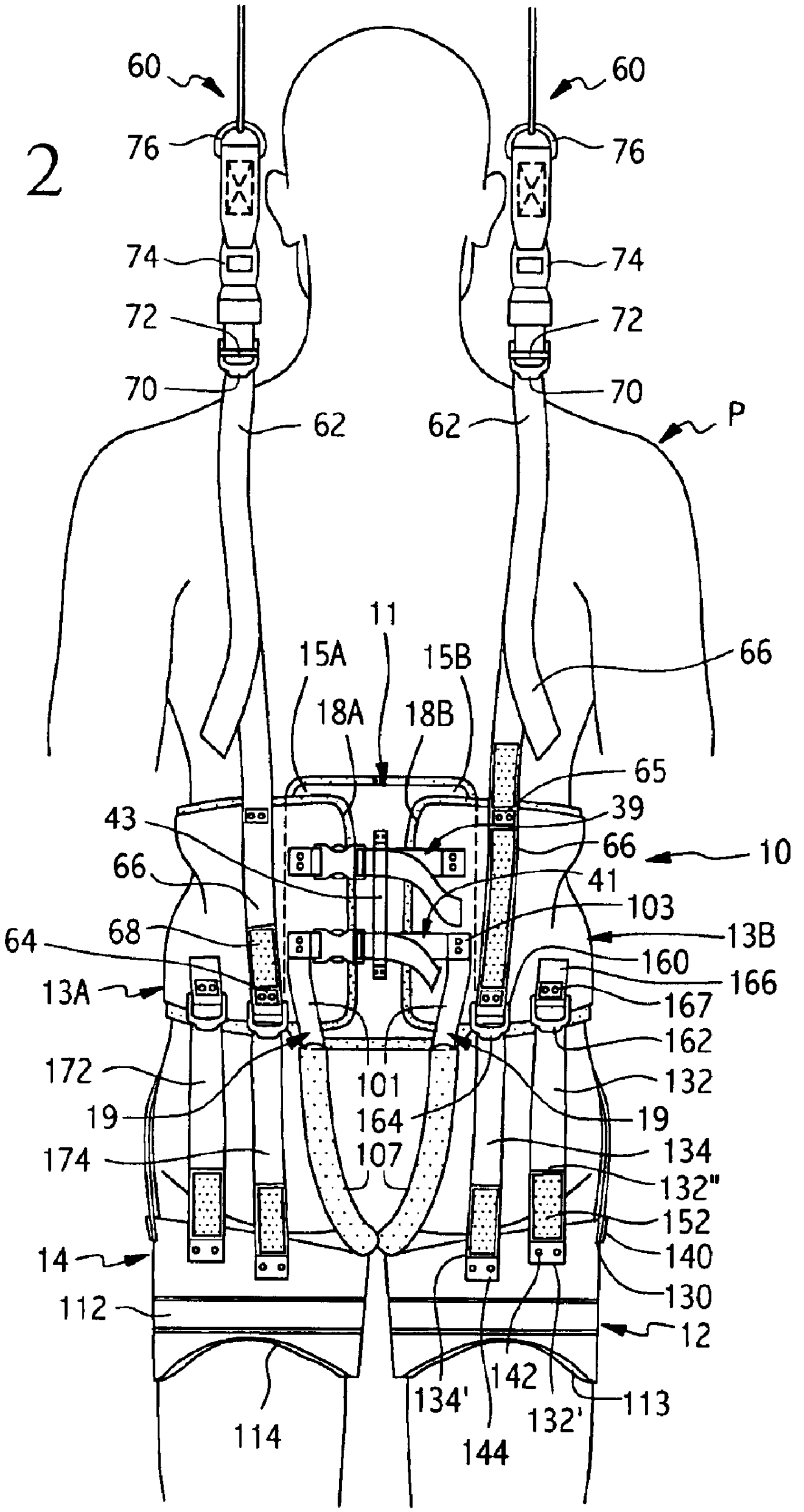
FIG. 2 is a rear view of one embodiment of the body harness mounted in operative position upon the body of a patient.

As discussed above, in one embodiment the body panels 13A and 13B of the torso support portion 10 each have a front free side 16A and 16B, respectively, and rear free side 18A and 18B, respectively, while the rear panel 11 has opposite free sides 15A and 15B. As seen in FIG. 1, when the torso support portion 10 is mounted on the patient in operative position, the parts of the body panels 13A and 13B adjacent to the front free sides 16A and 16B overlap one another. As can be seen in FIG. 2, when the torso support portion 10 is mounted on the patient in operative position, the parts of the body panels 13A and 13B adjacent to the rear free sides 18A and 18B do not overlap one another. As shown in FIG. 2, the parts of the body panel 13A adjacent to the rear side 18A overlap a portion of the rear panel 11 adjacent to the free side 15A and the parts of the body panel 13B adjacent to the rear side 18B overlap a portion of the rear panel 11 adjacent to the free side 15B. The amount of overlap will depend on the adjustment of the rear panel 11 relative to the body panels 13A and 13B. The amount of adjustment will depend on the circumference of the patient's torso, among other factors, and therefore will be variable between patients. It is possible that there will be no overlap between the body panels 13A and 13B and the rear panel 11. In such an embodiment, there will be a distance between the rear free side 18A of the body panel 13A and the free side 15A of the rear panel and a distance between the rear free side 18B and the free side 15B of the rear panel.

Thigh support portion 12 has opposite free sides 20 and 22, and thigh support portion 14 has opposite free sides 24 and 26. When the thigh support portions 12 and 14 are mounted on the patient in operative position, the free sides thereof are spaced a distance from one another. With this arrangement, pinching of the patient's skin is avoided.

Tightening straps are provided for tightening the torso support portion 10 about a patient's torso. The tightening straps also secure the parts of the body panels 13A and 13B adjacent to the front free sides 16A and 16B in an overlapping relationship to one another and secure the parts of the body panels 13A and 13B adjacent to the rear free sides 18A and 18B in their final relationship to the rear panel 11 (which relationship may be varied as discussed above). As shown in FIG. 1, two tightening straps, 32 and 34 are illustrated on the body panels 13A and 13B adjacent to the front free sides 16A and 16B. The number of tightening straps is selected to provide sufficient tightening to secure the torso portion 10 to the torso of the patient P. The number of tightening straps may be decreased to one or increased to more than two if desired. The orientation of the tightening straps may be either in the same direction or in the opposite direction. As shown in FIG. 2, two tightening straps, 39 and 41 are illustrated on the body panels 13A and 13B adjacent to the rear free sides 18A and 18B and extend across the rear panel 11. Rear panel 11 has a longitudinal strap 43 which movably secures the tightening straps 39 and 41 to the rear panel 11. The number of tightening straps is selected to provide sufficient tightening to secure the torso portion 10 to the torso of the patient P. The number of tightening straps may be decreased to one or increased to more than two if desired.

The orientation of the tightening straps may be either in the same direction or in the opposite direction.

The operation of the tightening straps can be seen in FIG. 3. The operation of the tightening straps 32, 34, 39 and 41 is essentially identical and a description of the operation for one can be applied to all. For simplicity the operation of strap 32 will be described in detail. Strap 32 has one end 32' fixed to the body panel 13A of the torso support portion 10 near the front free side 16A. In one embodiment, the fixed end 32 is secured by nut and bolt assemblies 36. Each of the assemblies 36 includes a bolt 92 extending inwardly through aligned holes in the strap 32 and the torso support portion 10. The inner end of the bolt is threaded into a threaded stem of a nut having a disc-like head 90 which engages the inner face of the inner layer 10" of the torso support portion (see FIG. 4 for an illustration of these assemblies in the thigh support 12). Such nut and bolt assemblies are of conventional construction and are referred to as a Chicago screw or binding screw assembly. Similar nut and bolt assemblies are utilized throughout the harness construction. In the case of assemblies 36, the bolt extends through a washer which engages the outer face of strap 32. It should be noted that other fastening assemblies can be used as is known to those of ordinary skill in the art.

The other end 32" of strap 32 is free and strap 32 has an intermediate portion between ends 32' and 32" and is releasably and adjustably secured to the body panel 13B of the torso support portion 10 as described below. In one embodiment illustrated in FIG. 3A, the outer face of strap 32 has a first portion 40 and a second portion 42 of a hook and loop fastener supported thereon. For example, portion 40 may comprise the hook portion and portion 42 may comprise the loop portion. These hook and loop portions are disposed at a portion of the strap which is intermediate the opposite ends 32' and 32". A fitting 46 is fixed to the body panel 13B of the torso support portion 10 near the opposite front free side 16B of the torso support portion by a nut and bolt assembly as described above, with fitting 46 pivotally supporting a metal loop 50. The intermediate portion of strap 32 passes through loop 50. It is apparent that when it is desired to tighten and secure the torso support portion in position, the free end of strap 32 is passed through loop 50 and then pulled as hard as desired. The strap is then doubled back on itself to engage fastener portions 40 and 42 with one another to secure the torso support in adjusted position.

In an alternate embodiment shown in FIG. 3B, the free end 32" engages a first portion 51 of a quick release buckle. The second portion 53 of the quick release buckle is pivotally fixed to a fitting 46 which is secured to the body panel 13B of the torso support portion 10 (such as by nut and bolt assemblies as described) near the free side 16B. The exact configuration of the quick release buckle is not critical to the present disclosure provided that the buckle allows reversible engagement and adjustment of the straps. The operation of such quick release buckles is well known in the art and the description below is provided as an example of one embodiment of the components of the quick release buckle. In the embodiment shown in FIG. 3B the first portion 51 comprises a flexible pronged element 51' and a retainer 51" with a bar 51''' disposed therein and the second portion 53 comprises a housing. The pronged element 51' reversibly interacts with the housing of the second portion 53 to allow the pronged element to be inserted and removed from the housing portion as is well known to those of ordinary skill in the art. Specifically, the housing 53 has an upper, lower and two side walls which define a central cavity for receiving the pronged element. The cavity of the housing is slightly less than the dimension of the pronged element 51', causing the pronged element 51' to be compressed slightly when inserted into the housing. The side walls each have an opening therein which allows the pronged element 51' to expand into the opening and thereby be secured in the housing as the pronged element 51' engages the openings in the side walls. As is obvious, by compressing the pronged element 51' and pulling on the strap 32, the pronged element 51' and the free end 32" can be removed from the housing. Furthermore, the retainer 51" adjustably receives the free end 32" and intermediate portions of the strap 32, allowing for adjustment of the strap 32. It is apparent that when it is desired to tighten and secure the torso support portion in position, the free end 32" and the intermediate portion of strap 32 is passed through retainer 51" and wrapped around the bar 51''' so that the strap 32 is doubled back on itself. The trap 32 is the pulled to tighten the strap and harness as desired. The strap may be secured as with a clip (designated 57) or similar device.

Straps 34, 39 and 41 are of similar construction to strap 32 and operate in a manner analogous to that of strap 32 and accordingly, no further discussion of straps 34, 39 or 41 is necessary. If the straps 32 and 34 and/or 39 and 41 are oriented in opposite directions, it allows a therapist to effectively tighten strap 32 and/or 39 in the opposite direction from which strap 34 and/or 41 is effectively tightened, so that the torso support portion can be adjusted from opposite sides of the patient. However, it is not necessary that straps 32 and 34 and/or 39 and 41 be placed in opposite orientations for the torso support portion 10 to be effectively tightened.

Four suspension strap means 60 are provided, these straps being identical in construction, and accordingly, similar reference numerals are applied to each of the straps means. Each suspension strap means includes a lower strap 62 having a lower end 63 fixed to the torso support portion by a pair of spaced metal plates 64 and 65 which are fixed to the torso support portion by nut and bolt assemblies as previously described. The opposite end 66 of each lower strap is free, and each lower strap includes an intermediate portion between the opposite ends thereof. Each lower strap includes separate hook and loop fastener portions 68 and 69 on the outer face of the strap adjacent the opposite ends thereof. For example, 68 may be the hook fastener portions and 69 may be the loop fastener portions.

Each suspension strap means also includes a metal loop 70 having a sliding metal bar 72 of conventional construction. The intermediate portion of the lower strap extends through the loop and is wrapped around the bar so that the bottom strap is doubled back on itself and the hook and loop portions are engaged with one another to hold the suspension strap means in adjusted position. It is apparent that the length of the lower strap between loop 70 and the torso support portion can be adjusted by unloading the lower strap and moving it through loop 70 until the desired position is reached whereupon the lower strap can be loaded to hold it in position.

Each suspension strap means also includes a quick-release buckle 74 as used in the seat belts on airplanes, this buckle having a first side which is pivotally connected to loop 70 and an opposite side which is connected to a connector member 76 such as a metal D-ring which is adapted to connect the harness to a powered gait orthosis device.

Two groin straps are provided, these straps being essentially identical in construction to one another and accordingly, similar reference numerals are applied to each of the groin straps. As shown in FIG. 2, each groin strap 19 has a first end 101 secured to the rear free sides 18A and 18B of the rear panel 11 by plates 103 and nut and bolt assemblies as described. The plates 103 may also secure portions of the lowermost tightening strap if desired. The second end 105 of the groin straps 19 is free and each groin strap 19 has an intermediate portion between ends 101 and 105. The groin straps may be adjustable secured to the front side of the body panels 13A and 13B using a cooperative adjustable buckle as described for strap 32 as shown in FIG. 1. Briefly, the free end 105 engages a first portion 107 of the cooperative adjustable buckle (shown best in FIG. 3B). The second portion 109 of the cooperative adjustable buckle is pivotally fixed to a fitting which is secured to the body panels 13A and 13B (such as by nut and bolt assemblies as described). The exact configuration of the cooperative, adjustable buckle is not critical to the present disclosure provided that the attachment element allows reversible engagement and adjustment. The cooperative adjustable buckle portions 107 and 109 operate as described for portions 51 and 53 described above, and therefore, no further description is needed. As is obvious, the groin straps may be adjusted as needed. Each groin strap 19 may further comprise a padding member 107 moveably secured thereto to increase the comfort to the patient P during use. Each groin strap 19 is placed through the legs of the patient P.

Figure 4:
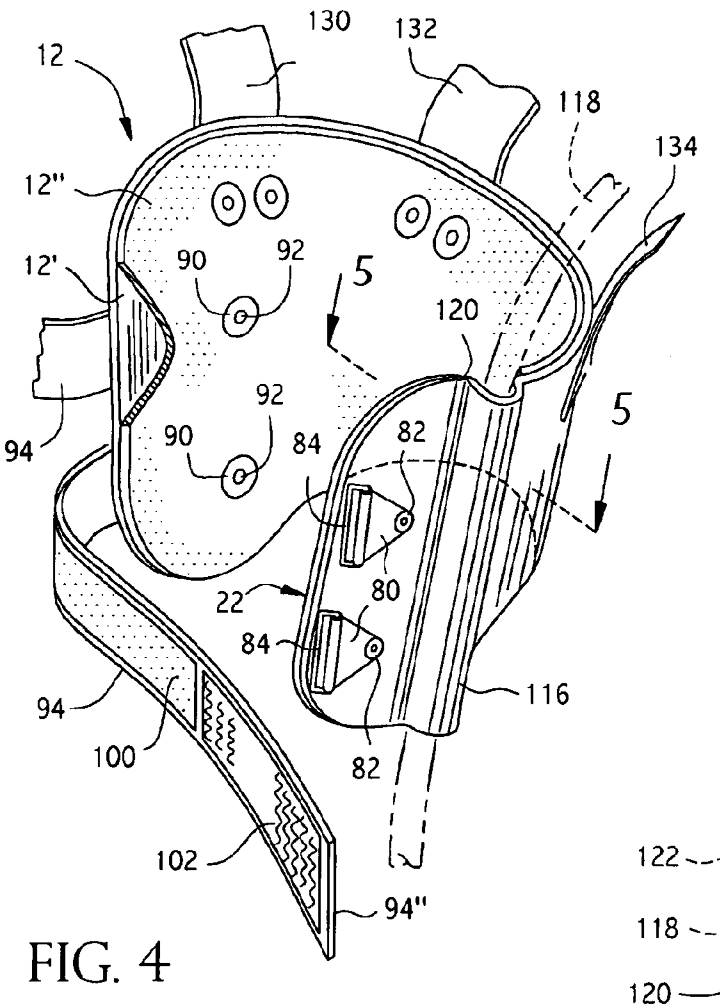
FIG. 4 is a top perspective view of the thigh support portion of the harness prior to mounting on a patient.
Figure 5:
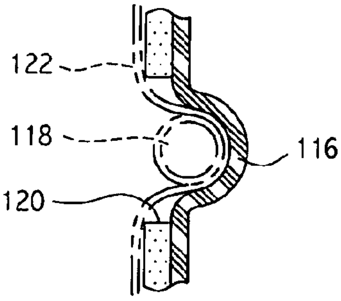
FIG. 5 is a cross-section through the thigh support portion taken along line 5—5 of FIG. 4.

The construction of thigh support portion 12 is seen in FIGS. 4 and 5, wherein it is seen in its normal relaxed position. The interior of portion 12 generally defines a frusto-conical configuration, or in other words it tapers downwardly and inwardly so that it will not tend to ride up on a patient's thigh when in use. A pair of similar fittings 80 are fixed to portion 12 adjacent free side 22 thereof by nut and bolt assemblies 82 similar to those previously described. A metal loop 84 is pivotally supported by each of fittings 80. A similar pair of fittings 86 as seen in FIG. 1 are similarly fixed to thigh support portion 12 adjacent free side 20 thereof, and each of such fittings pivotally supports a metal loop 88 similar to loops 84. The disc-like heads 90 of the nuts and the ends of the bolts 92 threaded thereinto of the nut and bolt assemblies fixing plastic fittings 86 to portion 12 are visible in FIG. 4.

A pair of tightening straps 94 are provided and each has one end 94' passing through an associated loop 88 and doubled back on itself and stitched in place to pivotally connect end 94' to the loop. The opposite end 94" of each strap 94 is free. An intermediate portion of each strap 94 is provided between the opposite ends thereof, and separate hook and loop fastening portions are disposed on one face thereof. A first fastening portion 100 may be a hook portion and a second fastening portion 102 may be a loop fastening portion.

When it is desired to tighten and secure thigh support portion 12 in place, the free ends of straps 94 are passed through loops 84 and doubled back on straps 94 so that the fastening portions thereof are in engagement with one another to secure the thigh support portion in operative position.

Thigh support portion 14 is of similar construction to thigh support portion 12 and is basically a mirror image thereof. A pair of tightening straps 106 are similar to straps 94 of thigh support portion 12 and are mounted and operate in the same manner as straps 94 except in the opposite direction. Therefore, no further description of the details of thigh support portion 14 is necessary.

As seen in FIG. 2, the rear side of thigh support portions 12 and 14 are provided with an outwardly facing hook and loop fastening portions 110 and 112 respectively. These fastening portions may be secured to the outer layer of the thigh support portions by suitable adhesive means. Each of fastening portions 110 and 112 may for example comprise loop portions which are adapted to engage hook portions on parts of a powered gait orthosis device so that motions of the orthosis device may be transmitted to the thigh support portions and thence to the thighs of the legs of a patient using the orthosis device. Thigh support portions 12 and 14 also have arcuate cutouts 113 and 114 respectively in the bottom edges of the rear sides thereof.

As seen in FIGS. 4 and 5, thigh support portion 12 differs from thigh support portion 14 in that the outer layer 12' includes an outwardly extending integral molded part 116 which is of generally semi-circular cross-section extending from the top edge to the bottom edge of thigh support portion 12 and which defines a channel for receiving a catheter 118 shown in phantom line in FIG. 5. A cutout 120 is formed in the inner layer 12" and also extends from the top edge to the bottom of thigh support portion 12 for receiving part of the catheter. A piece of fabric 122 is illustrated in FIG. 5 to show the manner in which the fabric of a pant leg as well as a catheter carried by a patient fits within the channel and cutout thereby preventing any damage to the catheter when the thigh support is tightened and secured around a patient's leg. It should be understood that there is no corresponding part 116 or cutout 118 in thigh support portion 14, and the inner and outer layers of thigh support 14 are continuous curves from one free side to the other free side thereof.

Thigh support portion 12 is connected to the torso support portion in depending relationship therefrom by three connecting straps 130, 132 and 134 the lower ends 130', 132' and 134' of which respectively are fixed to thigh support portion 12 by three plates 140, 142 and 144 and nut and bolt assemblies as previously described. The straps have opposite ends 130", 132" and 134" which are free. Each of the connecting straps has separate hook and loop fastening portions on one face thereof at an intermediate portion between the opposite ends thereof as described above. The fastening portions 152 and 154 adjacent the lower ends of connecting straps 132 and 134 can be seen in FIG. 2. A similar fastening portion (not shown) is provided on strap 130.

The fastening portions adjacent the free ends of straps 130, 132 and 134 are not visible in the drawings, but it will be understood that they are in facing contact with the previously mentioned fastening portions adjacent the lower ends of the straps when the connecting straps are doubled back on themselves as shown in FIGS. 1 and 2.

The intermediate portions between opposite ends of connecting straps 130, 132 and 134 pass through loops 160, 162 and 164 respectively, each of these loops having a sliding bar with the associated connecting strap wound therearound with each connecting strap being doubled back on itself and with the separate fastening portions thereon in contact with one another. This enables the position of thigh support portion 12 to be adjusted relative to the torso support portion in a well-known manner.

Loop 160 is pivotally supported by the lower end 63 of one of the suspension straps 62 as seen in FIG. 1. Loop 162 is pivotally supported by a short strap 166 fixed to the torso support portion by a plate 167 and nut and bolt assemblies as previously described. Loop 164 is pivotally supported by the lower end 63 of one of the suspension straps as seen in FIG. 2.

Thigh support portion 14 is connected to the torso support portion in depending relationship therefrom by three connecting straps 170, 172 and 174 which correspond to straps 130, 132 and 134 respectively of thigh support portion 12. Straps 170, 172 and 174 are of the same construction and operate in the same manner as straps 130, 132 and 134 discussed in connection with thigh support portion 12. Therefore, no further explanation is required regarding the construction of connecting straps 170, 172 and 174 and the manner in which they adjustably connect thigh support portion 14 to the torso support portion.

The body harness has been described with reference to a preferred embodiment. Obviously, various modifications, alternatives and other embodiments will occur to others upon reading and understanding this specification. It is the intention to include all such modifications, alternatives and other embodiments insofar as they come within the scope of the appended claims or equivalents thereof.

What is claimed is:

1. A body support harness for supporting a patient comprising, a torso support portion for fitting around a torso of a patient, said torso support portion comprising a first and a second body panel and a rear panel adjustably secured between the first and second body panels, a pair of thigh support portions for fitting around a thigh of the patient and adjustably connected to said torso support portion and depending therefrom, a plurality of suspension strap means for suspending said torso support portion, said first and second body panels each having a front free side and a rear free side, and said rear panel and thigh support portions each having a set of opposite free sides, and each of the torso support portion and thigh support portion being formed of an outer layer of hard relatively stiff molded plastic material of limited flexibility and an inner layer of relatively soft cushioning material for distributing the weight of a patient over a large area, a securing means for tightening and securing said torso support portion about said torso of a patient's body and a securing means for tightening and securing each of said thigh support portions about said thighs of a patient's body.

2. A harness as defined in claim 1 where at least one of the torso support portion and the pair of thigh support portions further comprise a removable liner comprising a inner layer of relatively soft cushioning material.

3. A harness as defined in claim 1 further comprising a plurality of groin straps adjustably secured to the torso support portion for stabilizing said torso support portion against upward movement of said torso support portion along the torso of the patient.

4. A harness as defined in claim 3 comprising a first groin strap and a second groin strap, each of the first and second groin straps having a first end and a second end, the first end of the first and second groin straps being fixed to said torso support portion in a spaced apart manner near the rear free sides of the first and second body panels, the second end of the first and second groin strap adjustably engaging a first portion of a quick release buckle, a second portion of the quick release buckle for receiving the first portion of the buckle, the second portions being pivotally supported by said torso support portion and being disposed in a spaced apart manner near the front free sides of the first and second body panels.

5. A harness as defined in claim 4 further comprising a padding member movably secured to the first and second groin straps.

6. A harness as defined in claim 1 wherein the free sides of each of said thigh support portions are spaced a substantial distance from one another when in operative position on the thigh of a patient.

7. A harness as defined in claim 1 wherein the parts of the torso support portion adjacent to the front free sides of the first and second body panels overlap one another when in an operative position on the torso of the patient.

8. A harness as defined in claim 1 wherein the parts of the torso support portion adjacent to the rear free sides of the first and second body panels overlap a portion of the rear panel adjacent to the opposite free sides of the rear panel when in an operative position on the torso of the patient.

9. A harness as defined in claim 1 wherein said suspension strap means are four in number, each of said suspension strap means including a lower strap having a lower end, an intermediate portion and an opposite end, said lower end being fixed to said torso support portion, said opposite end being free, said lower strap having separate hook and loop fastening portions on one face of said intermediate portion, a loop including a sliding bar, said intermediate portion extending through said loop and being wrapped around said bar, a quick-release buckle having opposite buckle sides, one of said buckle sides being connected to said loop, and a connector member being connected to the other of said buckle sides.

10. A harness as defined in claim 1 where the securing means for the torso support portion comprises a first set of tightening straps to tighten and secure the front free sides of the first and second body panels and a second set tightening straps to tighten and secure the back free sides of the first and second body panels and to adjustable secure the rear panel between the first and second body panels by engaging a retaining strap secured to the rear panel.

11. A harness as defined in claim 10 where the plurality of first tightening straps tighten and secure the torso support portion so that the parts of the torso support portion adjacent to the front free sides of the first and second body panels are in an overlapping relationship to one another when the torso support portion is in an operative position.

12. A harness as defined in claim 11 where each of said plurality of first tightening straps have opposite ends and an intermediate portion, one of said ends being fixed to said torso support portion near the front free side of one of the first or second body panel, the other end of each of said tightening straps being free, a plurality of loops, each of said loops being pivotally supported by said torso support portion for receiving one of said tightening straps, each of said loops being disposed near the front opposite free side of the torso support portion opposite the front free side near which the fixed end of the associated tightening strap is disposed and, each of said tightening straps having separate hook and loop fastening portions on one face thereof at said intermediate strap portion, each of said intermediate portions passing through one of said pivotally mounted loops.

13. A harness as defined in claim 11 where each of said plurality of first tightening straps have opposite ends and an intermediate portion, one of said ends being fixed to said torso support portion near the front free side of one of the first or second body panels, the other ends of said tightening straps adjustably engaging a first portion of a quick release buckle, a second portion of the quick release buckle for receiving the first portion of the buckle, the second portion being pivotally supported by said torso support portion and being disposed near the front free side of the torso support portion opposite the front free side near which the fixed end of the associated tightening strap is disposed.

14. A harness as defined in claim 10 where the plurality of second tightening straps tighten and secure the torso support portion so that the parts of the torso support portion adjacent to the rear free sides of the torso support portion overlap a portion of the rear panel adjacent to the opposite free sides of the rear panel when in an operative position on the torso of the patient.

15. A harness as defined in claim 14 where each of said plurality of second tightening straps comprise opposite ends and an intermediate portion, one of said ends being fixed to said torso support portion near the rear free side of one of the first or second body panel, the other end of each of said tightening straps being free, a loop being pivotally supported by said torso support portion for receiving said tightening strap, the loop being disposed near the rear free side of the torso support portion opposite the rear free side near which the fixed end of the associated tightening strap is disposed and, each of said tightening straps having separate hook and loop fastening portions on one face thereof at said intermediate strap portion, each of said intermediate portions passing through one of said pivotally mounted loops and through the retaining strap on the rear panel.

16. A harness as defined in claim 14 where each of said plurality of second tightening straps comprise opposite ends and an intermediate portion, one of said ends being fixed to said torso support portion near the rear free side of one of the first or second body panels, the other ends of said tightening straps adjustably engaging a first portion of a quick release buckle, a second portion of the quick release buckle for receiving the first portion of the buckle, the second portion being pivotally supported by said torso support portion and disposed near the rear free side of the torso support portion opposite the rear free side near which the fixed end of the associated tightening strap is disposed and said intermediate portion of said strap passing through the retaining strap on the rear panel.

17. A harness as defined in claim 8 wherein at least one of said plurality of first tightening straps is fixed to said torso support portion in a different orientation from a remainder of said tightening straps.

18. A harness as defined in claim 8 wherein at least one of said plurality of second tightening straps is fixed to said torso support portion in a different orientation from a remainder of said tightening straps.

19. A harness as defined in claim 8 wherein said plurality of first and second tightening straps are fixed to said torso support portion in the same orientation.

20. A harness as defined in claim 11 comprising two tightening straps.

21. A harness as defined in claim 14 comprising two tightening straps.

22. A harness as defined in claim 1 including a plurality of tightening straps for tightening each of said thigh support portions and securing the parts of each of the thigh support portions with the free sides thereof in spaced relationship to one another, each of said tightening straps of each of said thigh support portions having opposite ends and an intermediate portion, one of said ends being pivotally fixed to the associated thigh support portion near one of the free sides thereof, the other of said ends being free, a plurality of loops, each of said loops being pivotally supported by the associated thigh support portion positioned near the free side of the thigh support portion opposite the free side which the fixed end of the associated tightening strap is disposed, each of said tightening straps having separate hook and loop fastening portions on one face of said intermediate portion, each of said intermediate portions passing through one of said pivotally mounted loops.

23. A harness as defined in claim 1 wherein one of said thigh support portions has top and bottom edges and includes an outwardly extending part which defines a channel extending from said top edge to said bottom edge for receiving a catheter.

24. A harness as defined in claim 1 wherein said channel is defined by an integral molded portion of generally semicircular cross-section in said outer layer, and an adjacent cut-out being formed in said inner layer.

25. A harness as defined in claim 1 wherein each of said thigh support portions includes an outwardly facing hook and loop fastening portion secured to the outer layer thereof for fastening the thigh support portions to a powered gait orthosis device.

26. A harness as defined in claim 1 wherein each of said thigh support portions has three connecting straps for connecting a thigh support portion of the torso support portion, each of said connecting straps having a lower ends, an intermediate portion and an opposite end, said lower end being fixed to an associated thight support portion, said opposite end being free, each of said connecting straps having separate hook and loop fastening portions on one face thereof as said intermediate portion, said torso portion having a plurality of loops pivotally supported on the lower part thereof, the intermediate portion of each of said straps passing through one of said loops.

* * * * *